United States Patent
Salamone et al.

(10) Patent No.: US 7,629,386 B2
(45) Date of Patent: Dec. 8, 2009

(54) COMPOSITIONS CONTAINING TRIALKANOLAMINE ALKOXYLATE BUFFER

(75) Inventors: Joseph C. Salamone, Fairport, NY (US); Roya Nicole Borazjani, Fairport, NY (US); Daniel M. Ammon, Jr., Penfield, NY (US)

(73) Assignee: Bausch + Lomb Incorporated, Rochester, NY (US)

( * ) Notice: Subject to any disclaimer, the term of this patent is extended or adjusted under 35 U.S.C. 154(b) by 733 days.

(21) Appl. No.: 10/926,514

(22) Filed: Aug. 26, 2004

(65) Prior Publication Data

US 2006/0047006 A1    Mar. 2, 2006

(51) Int. Cl.
*A01N 33/08* (2006.01)
*A61K 31/13* (2006.01)

(52) U.S. Cl. .................................... 514/668
(58) Field of Classification Search ................ 514/668
See application file for complete search history.

(56) References Cited

U.S. PATENT DOCUMENTS 2,174,761 A * 10/1939 Schuette et al. ............... 558/26
4,820,352 A    4/1989 Riedhammer et al. ......... 134/30
5,500,186 A    3/1996 Mowrey-McKee et al. .... 422/28
6,143,244 A    11/2000 Xia et al.
6,274,133 B1 *  8/2001 Hu et al. ................... 424/78.04
6,319,464 B1   11/2001 Asgharian .................... 422/28
6,617,291 B1    9/2003 Smith
2003/0190258 A1 10/2003 Smith ......................... 422/28

FOREIGN PATENT DOCUMENTS

GB          1245237 A     9/1971
WO       WO97/28687 A     8/1997

OTHER PUBLICATIONS

Database CA Online!, Chemical Abstracts Service, Columbus, Ohio, US; Mar. 10, 2004, Bacneanu, George et al: "Disinfectant and detergent composition" XP002355568 retrieved from STN, Database accession No. 2004:191150.
RO 117 540 B1 (S.C. Chimcomplex S.A. Borzesti, Onesti, Rom) Apr. 30, 2002.

* cited by examiner

*Primary Examiner*—Frederick Krass
*Assistant Examiner*—Sean Basquill
(74) *Attorney, Agent, or Firm*—Joseph Barrera

(57) ABSTRACT

The use of compositions containing one or more antimicrobial agents with one or more trialkanolamine alkoxylate buffers to disinfect and/or preserve medical devices is described. Solutions containing one or more antimicrobial agents with one or more trialkanolamine alkoxylate buffers and methods of making and using the same are also described.

11 Claims, No Drawings

COMPOSITIONS CONTAINING TRIALKANOLAMINE ALKOXYLATE BUFFER

FIELD OF THE INVENTION

The present invention is directed toward the use of one or more trialkanolamine alkoxylate buffers in a lens care solution containing an antimicrobial agent to achieve enhanced disinfection and preservation. More particularly, the present invention is directed toward the use of one or more trialkanolamine alkoxylate buffers in combination with one or more biguanides to enhance disinfection and preservation of ophthalmic solutions and devices.

BACKGROUND OF THE INVENTION

Contact lenses in wide use today fall into three general categories: hard lenses formed from materials prepared by polymerization of acrylic esters such as poly(methyl methacrylate) (PMMA); rigid gas permeable (RGP) lenses formed from silicone (meth)acrylates and fluorosilicone methacrylates; and gel, hydrogel or like soft-type lenses. The hard and rigid-type lenses, because they are characterized by low vapor diffusion and absorb only minor amounts of aqueous fluids, have a lower tendency to bind ingredients used in contact lens care solutions. On the other hand, soft-type lenses have a greater tendency to bind active ingredients used in contact lens care solutions. Therefore, developing solutions designed for the treatment of soft-type lenses, whether made from the more traditional copolymers of 2-hydroxyethyl methacrylate (HEMA) or from the newer siloxane-containing hydrogel materials is especially challenging.

In the normal course of wearing contact lenses, tear film and debris consisting of proteinaceous, oily, sebaceous, and related organic matter have a tendency to deposit and build-up on lens surfaces. Many factors influence deposit formation, including patient to patient variation, lens material, care regimen, and environment. In general, relatively high water content ionic lens materials absorb more protein than relatively low water content or nonionic lens materials. As part of the routine care regimen, contact lenses must be cleaned to remove tear film deposits and debris. If deposits are not properly removed, both the wettability and optical clarity of the lenses are substantially reduced and wearer discomfort may result.

Further, contact lenses must also be disinfected to kill harmful microorganisms that may be present or grow on the lenses. Some of the most popular products for disinfecting lenses are multi-purpose solutions that can be used to clean, disinfect, and wet contact lenses, followed by direct insertion or placement on the eye, without rinsing. Obviously, the ability to use a single solution for contact lens care is an advantage. Such a solution, however, must be particularly gentle to the eye, since at least some of the solution will be on the lens when inserted or placed on the eye and will thereby come into direct contact with eye tissues.

British Patent Number 1,432,345 discloses contact lens disinfecting compositions containing a polymeric biguanide and a mixed phosphate buffer. Compositions as disclosed by this patent, however, have corneal staining values of 17 percent or more, far above that which is desirable for patient acceptability.

U.S. Pat. No. 6,143,244 discloses a method for treating contact lenses and compositions for such use. The method includes the use of an aqueous biguanide-containing disinfecting solution including an improved buffer system comprising a mixture of a phosphate and a borate buffer. Preferred embodiments of the invention include methods and compositions for simultaneously cleaning and disinfecting contact lenses.

U.S. Pat. No. 4,758,595 discloses a contact lens solution containing a poly(aminopropyl biguanide) (PAPB), also known as poly(hexamethylene biguanide) (PHMB), having enhanced efficacy when combined with a borate buffer. These disinfecting and preservative solutions are especially noteworthy for their broad spectrum of bactericidal and fungicidal activity at low concentrations coupled with very low toxicity when used with soft-type contact lenses. Compositions containing PHMB and borate have been commercialized in various products including multi-purpose solutions, at levels of about 1 ppm or less for use with soft contact lenses.

The fact that multipurpose solutions are designed for use as a wetting agent, without rinsing, means that the solution must be ophthalmically safe for eye contact. This limits, to some extent the type and concentration of both cleaning agents and antimicrobial agents or biocides that can be employed in the solution. For example, as can be readily understood, biocides or cleaners in a shampoo product may not be suitable for ophthalmic use. A challenge has been to develop a formula that is, on the one hand, maximally efficacious and, on the other hand, sufficiently gentle to be not only safe, but comfortable for in-the-eye use.

With conventional contact lens cleaners or disinfectants, including multipurpose solutions, lens wearers typically need to digitally or manually rub the contact lenses, typically between a finger and palm or between fingers, during treatment of the contact lenses. The necessity for the daily "rubbing" of contact lenses adds to the time and effort involved in the daily care of contact lenses. Many contact lens wearers dislike having to perform such a regimen or consider it to be an inconvenience. Some wearers may be negligent in the proper "rubbing" regimen, which may result in contact lens discomfort and other problems. Sometimes rubbing, if performed too rigorously, which is particularly apt to occur with beginning lens wearers, may damage the lenses. This can be problematic when a replacement lens is not immediately available. Some wearers may be negligent in the proper "rinsing" regimen, which may result in contact lens discomfort and other problems.

Contact lens solutions that qualify as a "Chemical Disinfecting Solution" do not require rubbing to meet biocidal performance criteria for destroying representative bacteria and fungi as established by the U.S. Food and Drug Administration (FDA) under the Premarket Notification (510K) Guidance Document for Contact Lens Care Products, May 1, 1997. In contrast, contact lens solutions that qualify as a "Chemical Disinfecting System" do require a rubbing regimen to pass biocidal performance criteria. Traditionally, multipurpose solutions used for disinfecting and wetting or for disinfecting, cleaning and wetting qualify as Chemical Disinfecting Systems, but not as Chemical Disinfecting Solutions.

Traditional contact lens solutions may depend on the rubbing regimen, not only for efficacious disinfection, but also for efficacious cleaning. Thus, in order to develop a contact lens care solution that would provide efficacious cleaning without a rubbing or rinsing regimen, as opposed to "rub and rinse" and/or "no rub with rinse" regimens for cleaning, would require improved cleaning efficacy while still being sufficiently gentle for in-the-eye use.

It would be desirable to obtain a multipurpose contact lens solution that would provide increased cleaning efficacy. It would likewise be desirable to obtain improved cleaning efficacy while maintaining both biocidal efficacy of the solution and low order toxicity of the solution to eye tissue. Desirable solution low order toxicity to eye tissue is such that after the solution is used to treat a contact lens, the lens can be subsequently placed on the eye without rinsing the solution from the lens. While still more challenging to develop, it would also be desirable to obtain a solution that exhibits both efficacious cleaning and disinfection of a contact lens, without requiring a rubbing or rinsing regimen, or at least not inherently or invariably requiring rubbing and rinsing for acceptable performance. Such solution would allow direct placement of the contact lens on an eye following soaking in the solution and/or rinsing and rewetting with the solution.

SUMMARY OF THE INVENTION

The present invention relates to compositions useful for no-rub, with or without rinse, cleaning of contact lenses, for disinfecting medical devices such as contact lenses, for preserving solutions such as ophthalmic solutions, pharmaceuticals, artificial tears and comfort drops against microbial contamination, and for preserving medical devices such as contact lenses. Compositions of the present invention formulated into no-rub, with or without rinse, contact lens cleaning solutions eliminate the need for user rubbing of the contact lens during cleaning and provides enhanced, rapid disinfection of the contact lens. For purposes of the present invention, "rapid disinfection" is defined as microorganism reduction of at least one log in about one hour. No-rub cleaning and rapid disinfection of contact lenses leads to higher user compliance and greater universal appeal than traditional contact lens disinfecting and cleaning solutions.

Compositions of the present invention useful in the manufacture of disinfecting and preserving solutions comprise one or more antimicrobial agents and one or more trialkanolamine alkoxylate buffers. When combined with one or more suitable surfactants, such biocompatible solutions exhibit enhanced cleaning efficacy and enhanced biocidal efficacy. The present invention includes methods for treating contact lenses using such solutions and methods for making such solutions.

A method of using a no-rub, with or without rinse, contact lens cleaning solution of the present invention involves contacting a lens with an aqueous solution having a pH of about 5 to 8 comprising an effective amount of at least one antimicrobial agent, and about 0.001 percent to about 5 percent by weight of one or more trialkanolamine alkoxylate buffers, and about 0.001 percent to about 6 percent by weight of one or more suitable surfactants.

The subject compositions are effective in the manufacture of disinfecting systems that are non-toxic, simple to use and do not cause ocular irritation.

Accordingly, it is an object of the present invention to provide compositions useful in the manufacture of ophthalmic disinfecting systems.

Another object of the present invention is to provide compositions effective in the disinfection of medical devices.

Another object of the present invention is to provide compositions useful in ophthalmic systems for disinfecting contact lenses.

Another object of the present invention is to provide compositions useful as packaging solutions for contact lenses and intraocular lenses.

Another object of the present invention is to provide compositions useful as buffered solutions of ophthalmic drugs.

Another object of the present invention is to provide buffered solutions for dry eye formulations.

Another object of the present invention is to enhance the biocidal activity of cationic biocides.

Another object of the present invention is to inhibit the deposition of cationic biocides on a biomaterial surface through competitive interaction with a larger concentration of trialkanolamine alkoxylate buffer.

Another object of the present invention is to provide enhanced stability against protein denaturation on a biomaterial surface.

Another object of the present invention is to provide compositions useful in preserving ophthalmic systems from microbial contamination.

Another object of the present invention is to provide compositions useful in ophthalmic systems for disinfecting contact lenses with reduced or eliminated eye irritation.

Another object of the present invention is to provide a method of making compositions useful in ophthalmic systems.

Still another object of the present invention is to provide a method of making compositions useful as disinfecting and preservative agents.

These and other objectives and advantages of the present invention, some of which are specifically described and others that are not, will become apparent from the detailed description and claims that follow.

DETAILED DESCRIPTION OF THE INVENTION

Compositions of the present invention can be used with all contact lenses such as conventional hard and soft-type lenses, as well as rigid and soft gas permeable lenses. Such suitable lenses include both hydrogel and non-hydrogel lenses, as well as silicone and fluorine-containing lenses. Of primary interest are soft lenses fabricated from a material having a proportion of hydrophilic repeat units such that the water content of the lens during use is at least 20 percent by weight. The term "soft contact lens" as used herein generally refers to those contact lenses that readily flex under small amounts of force. Typically, soft contact lenses are formulated from polymers having a certain proportion of repeat units derived from monomers such as 2-hydroxyethyl methacrylate and/or other hydrophilic monomers, typically crosslinked with a crosslinking agent. However, newer soft lenses, especially for extended wear, are being made from high-Dk siloxane- and fluorosiloxane-containing materials.

Compositions of the present invention comprise one or more antimicrobial agents such as but not limited to biguanides as a disinfectant or preservative, and one or more trialkanolamine alkoxylate buffers as a buffering agent. It is surprising that the subject compositions exhibit excellent disinfecting and/or preservative effect without the aid of borate, which is contrary to the teachings of U.S. Pat. No. 4,758,595.

Compositions of the present invention are useful for disinfecting and cleaning medical devices, particularly those soiled with proteinaceous matter. Compositions of the present invention are also useful in contact lens care solutions for disinfecting contact lenses. Compositions of the present invention are preferably in solution in sufficient concentration to destroy harmful microorganisms on the surface of a contact lens within the recommended minimum soaking time. The recommended minimum soaking time is included in the package instructions for use of the solution. The term "disinfecting solution" as used herein does not exclude the possibility that the solution may also be useful as a preserving solution, or that the disinfecting solution may be useful for other purposes such as daily cleaning, rinsing, and storage of contact lenses, depending on the particular formulation containing the subject compositions. Additionally, compositions of the present invention can be used in conjunction with other known disinfecting or preserving compounds if desired.

Compositions of the present invention in solution are physiologically compatible. Specifically, the solutions are "ophthalmically safe" for use with a contact lens, meaning that a contact lens treated with a solution of the present invention is generally suitable and safe for direct placement on the eye without rinsing. The solution is safe and comfortable for daily contact with the eye via a contact lens that has been wetted with the solution. An ophthalmically safe solution has a tonicity and pH that is compatible with the eye and comprises materials, and amounts thereof, that are non-cytotoxic according to ISO (International Standards Organization) standards and U.S. FDA (Food and Drug Administration) regulations. The solution should be sterile in that the absence of microbial contaminants in the product prior to release must be statistically demonstrated to the degree necessary for such products.

As noted above, compositions of the present invention include one or more antimicrobial agents present in a total amount of from approximately 0.000001 to approximately 5.0 percent by weight based on the total weight of the composition. Said one or more antimicrobial agents are preferably present in compositions of the present invention from about 0.00001 to about 5.0 weight percent, more preferably from about 0.00001 to about 1.0 weight percent and most preferably from about 0.00003 to about 0.5 weight percent. Suitable antimicrobial agents include for example but are not limited to 1,1'-hexamethylenebis[5-(p-chlorophenyl)biguanide] (Chlorhexidine) or water soluble salts thereof, 1,1'-hexamethylenebis[5-(2-ethylhexyl)biguanide](Alexidine) or water soluble salts thereof, poly(hexamethylene biguanide) or water soluble salts thereof, polyquaternium-1, ionene polymers and quaternary ammonium esters. Biguanides are described in U.S. Pat. Nos. 5,990,174; 4,758,595 and 3,428,576, each incorporated herein in its entirety by reference. The preferred antimicrobial agents due to their ready commercial availability are poly(aminopropyl biguanide) (PAPB), also commonly referred to as poly(hexamethylene biguanide) (PHMB), and 1,1'-hexamethylenebis[5-(2-ethylhexyl)biguanide](Alexidine).

Compositions of the present invention likewise include one or more trialkanolamine alkoxylate buffers, of the generalized structure illustrated in Formula 1 below:

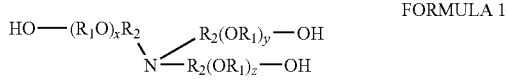

FORMULA 1 wherein the $R_1$ groups may be the same or different $C_{1-6}$ alkylene groups such as for example but not limited to methylene, ethylene or propylene; the $R_2$ groups may be the same or different $C_{1-6}$ alkylene groups such as for example but not limited to methylene, ethylene or propylene; and x, y and z may be the same or different selected from the group consisting of integers from 1 to 100.

One or more trialkanolamine alkoxylate buffers are present in the subject compositions in a total amount of from approximately 0.02 to approximately 3.0 percent by weight based on the total weight of the composition. Suitable trialkanolamine alkoxylate buffers include for example but are not limited to triethanolamine ethoxylate buffers where x=1-100, y=1-100 and z=1-100, with a preference of x=1-50, y=1-50 and z=1-50, and more preferably with x=1-10, y=1-10 and z=1-10, with the greatest preference of x=1-2, y=1-2 and z=1-2. Such compounds are available as a mixture from Sigma-Aldrich, catalog number 41,658-4 (Sigma-Aldrich Corporation, Milwaukee, Wis.).

Compositions of the present invention when formulated as a cleaning solution include a total amount of from about 0.001 to about 6 percent by weight of one or more surfactants having known advantages in terms of cleaning efficacy and comfort. Suitable surfactants include for example but are not limited to polyethers based upon poly(ethylene oxide)-poly(propylene oxide)-poly(ethylene oxide), i.e., (PEO-PPO-PEO), or poly (propylene oxide)-poly(ethylene oxide)-poly(propylene oxide), i.e., (PPO-PEO-PPO), or a combination thereof. PEO-PPO-PEO and PPO-PEO-PPO are commercially available under the trade names Pluronics™, R-Pluronics™, Tetronics™ and R-Tetronics™ (BASF Wyandotte Corp., Wyandotte, Mich.) and are further described in U.S. Pat. No. 4,820,352 incorporated herein in its entirety by reference. Suitable surfactants for use in the present composition should be soluble in the lens care solution, not become turbid, and should be non-irritating to eye tissues.

Compositions of the present invention may optionally include one or more water-soluble viscosity agents in the subject composition. Because of the demulcent effect of viscosity agents, the same have a tendency to enhance the lens wearer's comfort by means of a film on the lens surface cushioning impact against the eye. Suitable viscosity agents include for example but are not limited to water-soluble cellulose polymers such as hydroxyethyl, hydroxypropyl or hydroxypropylmethyl cellulose, guar, hydroxyethyl guar, hydroxypropyl guar, hydroxypropylmethyl guar, poly(N-vinylpyrrolidone), poly(vinyl alcohol), poly(ethylene glycol), poly(ethylene oxide) and the like. Viscosity agents may be employed in amounts ranging from about 0.01 to about 4.0 weight percent or less.

Compositions of the present invention may likewise include one or more buffers, or a buffering system in addition to the one or more trialkanolamine alkoxylate buffers, to adjust the final pH of the solution. Suitable buffers include for example but are not limited to citrate buffers, phosphate buffers, borate buffers, tris(hydroxymethyl)aminomethane (Tris) buffers, sodium bicarbonate, as well as Good Buffers such as but not limited to N,N'-bis(2-hydroxyethyl)glycine (BICIN), 2-[bis(2-hydroxyethyl)amino]-2-(hydroxymethyl)-1,3-propanediol (BISTRIS), 2-(cyclohexylamino)ethane-2-sulfonic acid (CHES), N-2-(hydroxyethyl)piperazine-N'-2-ethanesulfonic acid (HEPES), N-(2-hydroxyethyl)piperazine-N'-3-propanesulfonic acid (HEPPS), morpholinoethanesulfonic acid (MES), morpholinopropanesulfonic acid (MOPS), piperazine-N,N'-bis(2-ethanesulfonic acid) (PIPES), N-tris(hydroxymethyl)methyl-2-aminoethanesulfonic acid (TES), N-tris(hydroxymethyl)methyl-3-aminopropanesulfonic acid (TAPS), and N-tris(hydroxymethyl)methylglycine (TRICINE), and combinations thereof. Good Buffers (Good N. E. et al, (1966) Biochemistry, 5, 467-477) are non-toxic to cells, are not absorbed through cell membranes and feature pKa values at or near physiological pH. The pH of lens care solutions of the present invention is preferably maintained within the range of 5.0 to 8.0, more preferably about 6.0 to 8.0, most preferably about 6.5 to 7.8.

Compositions of the present invention may likewise include one or more tonicity agents to approximate the osmotic pressure of normal lachrymal fluids which is equivalent to a 0.9 percent solution of sodium chloride or 2.5 percent glycerin solution. Examples of suitable tonicity agents include but are not limited to zinc chloride, sodium chloride, potassium chloride, dextrose, mannose, glycerin, propylene glycol, calcium chloride and magnesium chloride. These agents are typically used individually in amounts ranging from about 0.01 to 2.5 percent w/v and preferably, from about 0.2 to about 1.5 percent w/v. Preferably, the tonicity agent is employed in an amount to provide a final osmotic value of 200 to 450 mOsm/kg and more preferably between about 205 to about 350 mOsm/kg, and most preferably between about 210 to about 320 mOsm/kg.

Compositions of the present invention may likewise include one or more sequestering agents to bind metal ions, which in the case of ophthalmic solutions, might otherwise react with protein deposits and collect on contact lenses. Suitable sequestering agents include for example but are not limited to ethylenediaminetetraacetic acid (EDTA) and its salts, gluconic acid, citric acid, tartaric acid and their salts, such as sodium salts. Sequestering agents are preferably used in amounts ranging from about 0.01 to about 0.2 weight percent.

Compositions of the present invention may optionally include one or more cationic polysaccharides. One or more cationic polysaccharides are present in the subject compositions in a total amount of from approximately 0.001 to approximately 0.5 percent by weight based on the total weight of the composition, but more preferably from about 0.005 to about 0.05 percent by weight. Suitable cationic polysaccharides for use in compositions of the present invention include for example but are not limited to variations of Polyquaternium-10 such as for example but not limited to Polymer JR 125™ (Dow Chemical Company, Midland, Mich.) having a 2 percent solution viscosity of 75-125 cPs and 1.5 to 2.2 percent nitrogen, Polymer JR 400™ (Dow Chemical Company) having a 2 percent solution viscosity of 300 to 500 cPs and 1.5 to 2.2 percent nitrogen, Polymer JR 30 M™ (Dow Chemical Company) having a 1 percent solution viscosity of 1,000 to 2,500 cPs and 1.5 to 2.2 percent nitrogen, Polymer LR 400™ (Dow Chemical Company) having a 2 percent solution viscosity of 300 to 500 cPs and 0.8 to 1.1 percent nitrogen, Polymer LR 30M™ (Dow Chemical Company) having a 1 percent solution viscosity of 1,250 to 2,250 cPs and 0.8 to 1.1 percent nitrogen, and Polymer LK™ (Dow Chemical Company) having a 2 percent solution viscosity of 300 to 500 cPs and 0.8 to 1.1 percent nitrogen. The preferred cationic polysaccharide for use in the present invention is Polymer JR 125™ or Polymer JR 400™.

Compositions of the present invention may likewise include one or more water-soluble carbohydrates. Such carbohydrates are present in the subject compositions in a total amount of from approximately 0.01 to approximately 10.0 percent by weight based on the total weight of the composition, but more preferably from about 0.05 to about 5.0 percent by weight. Suitable carbohydrates for use in compositions of the present invention include for example but are not limited to monosaccharides, disaccharides, oligosaccharides and polysaccharides. Suitable monosaccharides include for example but are not limited to allose, altrose, glucose, mannose, gulose, idose, galactose, talose, ribose, arabinose, xylose and lyxose. Examples of suitable disaccharides are sucrose and trehalose. Suitable oligosaccharides, composed of two to eight units of monosaccharide, and polysaccharides, composed of more than eight units of monosaccharide, include for example but are not limited to agar, agarose, guar gum, hydroxypropylguar, hydroxypropylmethylguar, hydroxyethylguar, carboxymethylguar, gum arabic, dextran, locust bean, alginates, asafetida, gum benzoin, carrageenans, carob, colophone, galbanum, gum damar, gum cassia, hydroxyethylcelluose, hydroxypropylcellulose, hydroxypropylmethylcellulose, methylcellulose, carboxymethylcellulose, gum chicle, gum elemi, gum gambodge, gum rosin, gum sandarac, gum tara, gum terpentine, gum tragacanth, xanthan gum, gum yucca, pectin, gellen gum, hyaluronic acid, chondroitin sulfate, gum ghatti, gum guaiac, gum guaiac, gum guarana, gum guttae, gum karaya, gum konjac, gum mastix, gum myrrh and gum olibanum.

The subject compositions may likewise include a wetting agent, to facilitate the composition wetting the surface of a contact lens. Within the art, the term "humectant" is also commonly used to describe these materials. A first class of wetting agents are polymer wetting agents. Examples of suitable wetting agents include for example but are not limited to poly(vinyl alcohol) (PVA), poly(N-vinylpyrrolidone) (PVP), water-soluble cellulose derivatives such as hydroxypropylmethyl cellulose and poly(ethylene glycol). Water-soluble cellulose derivatives and PVA may be used to also increase viscosity of the composition, and offer this advantage, if desired. Specific cellulose derivatives include for example but are not limited to hydroxypropyl methyl cellulose, carboxymethyl cellulose, methyl cellulose, hydroxyethyl cellulose, and cationic cellulose derivatives. As disclosed in U.S. Pat. No. 6,274,133, cationic cellulosic polymers also help prevent accumulation of lipids and proteins on a hydrophilic lens surface. Such cationic cellulosic polymers include for example but are not limited to water soluble polymers commercially available under the CTFA (Cosmetic, Toiletry, and Fragrance Association) designation Polyquaternium-10, including the cationic cellulosic polymers available under the trade name UCARE® Polymers from Amerchol Corp., Edison, N.J. Generally, these cationic cellulose polymers contain quaternized N,N-dimethylamino groups along the cellulosic polymer chain.

Another suitable class of wetting agents is non-polymeric wetting agents. Examples include glycerin, propylene glycol, and other non-polymeric diols and glycols.

The specific quantities of wetting agents used in the present invention will vary depending upon the application. However, the wetting agents will typically be included in an amount from about 0.01 to about 5 weight percent, preferably from about 0.1 to about 2 weight percent.

The trialkanolamine alkoxylate-buffered compositions of the present invention are described in still greater detail in the examples that follow.

EXAMPLE 1

Preparation of Trialkanolamine Alkoxylate-Buffered Compositions

A test was conducted to study the microbiocidal efficacy of solutions prepared according to the present invention. The test solutions are identified below in Table 1.

TABLE 1

Trialkanolamine Alkoxylate-Buffered Test Solutions

| Ingredients (w/w %) | A | B | C |
| --- | --- | --- | --- |
| TEAE | 1 | 1 | 1 |
| Pluronic F38 | 1 | 1 | 1 |
| Tetronic 908 | 1 | 1 | 1 |
| PVP-30K | 1 | 1 | 1 |
| EDTA | 0.025 | 0.025 | 0.025 |
| Glycerin | 1 | 1 | 0.722 |
| Polymer JR 30 M | 0.02 | 0.02 | 0.02 |
| Trehalose | 0.2 | 0.2 | 0 |
| Alexidine (407 ppm) | 4 | 4 | 4.5 |
| PHMB (112 ppm) | 0.7 ppm | 0 | 0 |

TABLE 1-continued

Trialkanolamine Alkoxylate-Buffered Test Solutions

| Ingredients (w/w %) | A | B | C |
|---|---|---|---|
| Osmolality (mOsm/Kg) | 210 | 212 | 185 |
| pH | 7.22 | 7.23 | 7.15 |

TEAE = Triethanolamine ethoxylated buffer
PVP-30K = Poly(N-vinylpyrrolidone)
EDTA = Ethylenediaminetetraacetic acid
Polymer JR 30 M = Polyquaternium -10

EXAMPLE 2

Biocidal Stand-Alone Testing of Trialkanolamine Alkoxylate-Buffered Compositions The antimicrobial efficacy of each of the solutions for the chemical disinfection of contact lenses was evaluated. Microbial challenge inoculums were prepared using *Pseudomonas aeruginosa* (ATCC 9027), *Staphylococcus aureus* (ATCC 6538), *Serratia marcescens* (ATCC 13880), *Candida albicans* (ATCC 10231) and *Fusarium solani* (ATCC 36031). The test organisms were cultured on appropriate agar and the cultures were harvested using sterile Dulbecco's Phosphate Buffered Saline plus 0.05 percent weight/volume polysorbate 80 (DPBST) or a suitable diluent and transferred to a suitable vessel. Spore suspensions were filtered through sterile glass wool to remove hyphal fragments. *Serratia marcescens*, as appropriate, was filtered through a 1.2 micron filter to clarify the suspension. After harvesting, the suspension was centrifuged at no more than 5000×g for a maximum of 30 minutes at 20 to 25 degrees Celsius. The supernatent was poured off and resuspended in DPBST or other suitable diluent. The suspension was centrifuged a second time, and resuspended in DPBST or other suitable diluent. All challenge bacterial and fungal cell suspensions were adjusted with DPBST or other suitable diluent to $1\times10^7$ to $1\times10^8$ cfu/mL. The appropriate cell concentration may be estimated by measuring the turbidity of the suspension, for example, using a spectrophotometer at a preselected wavelength, for example 490 nm. One tube was prepared containing a minimum of 10 mL of test solution per challenge organism. Each tube of the solution to be tested was inoculated with a suspension of the test organism sufficient to provide a final count of $1\times10^5$ to $1\times10^6$ cfu/mL, the volume of the inoculum not exceeding 1 percent of the sample volume. Dispersion of the inoculum was ensured by vortexing the sample for at least 15 seconds. The inoculated product was stored at 10 to 25 degrees Celsius. Aliquots in the amount of 1.0 mL were taken of the inoculated product for determination of viable counts after certain time periods of disinfection. The time points for the bacteria were, for example, 1, 2, 3, 4 and 24 hours when the proposed regimen soaking time was four hours for 25%, 50%, 75%, 100% and 400% soaking time. The suspension was mixed well by vortexing vigorously for at least 5 seconds. The 1.0 mL aliquots removed at the specified time intervals were subjected to a suitable series of decimal dilutions in validated neutralizing media. The suspensions were mixed vigorously and incubated for a suitable period of time to allow for neutralization of the microbial agent. The viable count of organisms was determined in appropriate dilutions by preparation of triplicate plates of tryptic soy agar (TSA) for bacteria and Sabouraud dextrose agar (SDA) for mold and yeast. The bacterial recovery plates were incubated at 30 to 35 degrees Celsius for two to four days. The yeast recovery plates were incubated at 20 to 30 degrees Celsius for two to four days. The mold recovery plates were incubated at 20 to 25 degrees Celsius for three to seven days. The average number of colony forming units was determined on countable plates. Countable plates refer to 30 to 300 cfu/plates for bacteria and yeast, and 8 to 80 cfu/plates for mold except when colonies are observed only for the $10^0$ or $10^{-1}$ dilution plates. The microbial reduction was then calculated at the specified time points and recorded as set forth below in Table 2.

TABLE 2

Biocidal Stand-Alone Test Results
(Log Reduction After Exposure of Test Solutions to 10 Percent Organic Soil)

| Agent | Exposure | A | B | C |
|---|---|---|---|---|
| S. aureus | 1 hour | >4.7 | >4.6 | >5.1 |
|  | 4 hour | >4.7 | >4.6 | >5.1 |
| P. aeruginosa | 1 hour | >5.0 | >4.6 | >4.9 |
|  | 4 hour | >5.0 | >4.6 | >4.9 |
| S. marcescens | 1 hour | >4.9 | 4.7 | 3.8 |
|  | 4 hour | >4.9 | >4.7 | >4.7 |
| C. albicans | 1 hour | >5.0 | >4.9 | >5.0 |
|  | 4 hour | >5.0 | >4.9 | >5.0 |
| F. solani | 1 hour | 3.1 | 3 | >4.6 |
|  | 4 hour | 3.3 | >4.4 | >4.6 |

In order to demonstrate the suitability of the medium used for growth of test organisms and to provide an estimation of the initial inoculum concentration, inoculum controls were made by dispersing an identical aliquot of the inoculum into a suitable diluent, for example DPBST, using the same volume of diluent used to suspend the organism listed above. Following inoculation in a validated neutralizing broth and incubation for an appropriate period of time, the inoculum control must be between $1.0\times10^5$ to $1.0\times10^6$ cfu/mL.

The test solutions were evaluated based on the performance requirement referred to as the "Stand-Alone Procedure for Disinfecting Products" (Stand-Alone Test) and is based on the Disinfection Efficacy Testing for contact lens care products under the Premarket Notification (510(k)) Guidance Document for Contact Lens Care Products dated May 1, 1997, prepared by the U.S. Food and Drug Administration, Division of Ophthalmic Devices. This performance requirement does not contain a rub procedure. This performance requirement is comparable to current ISO standards for disinfection of contact lenses (revised 1995). The Stand-Alone Test challenges a disinfecting product with a standard inoculum of a representative range of microorganisms and establishes the extent of viability loss at predetermined time intervals comparable with those during which the product may be used. The primary criteria for a given disinfection period, corresponding to a potential minimum recommended disinfection period, is that the number of bacteria recovered per mL must be reduced by a mean value of not less than 3.0 logs within the given disinfection period. The number of mold and yeast recovered per ml must be reduced by a mean value of not less than 1.0 log within the minimum recommended disinfection time with no increase at four times the minimum recommended disinfection time.

EXAMPLE 3

Regimen Testing of Trialkanolamine Alkoxylate-Buffered Compositions

A four-hour no rub and no rinse (NR/NR) regimen using 10 ml of sample solution with a 10 second shaking step (ss) and a four-hour no rub and no rinse (NR/NR) regimen using 10 ml of sample solution with no shaking step (ns) was conducted on Focus™ Monthly (CIBA Vision, Basel, Switzerland) Group IV lenses (Gr IV-A), and tested using *Candida albicans* ATCC 10231. The test results for the regimens are set forth below in Table 3.

TABLE 3

Efficacy of Test Solutions in No Rub/No Rinse (NR/NR) Regimen Testing

| | TEST SOLUTION | | |
|---|---|---|---|
| | A | B | C |
| NR/NR Regimen 4 Hr soak/10 ml/10 ss (Gr IV-A) | | | |
| *Candida albicans* (CFU) | 0, 0, 0 | 0, 0, 0 | 0, 0, 0 |
| NR/NR Regimen 4 Hr soak/10 ml/ns (Gr IV-A) | | | |
| *Candida albicans* (CFU) | ND | 2, 3, 0 | ND |

<10 CFU = test passage
>10 CFU = test failure
CFU = colony forming units
ND = no data Compositions of the present invention comprising a disinfecting amount of one or more antimicrobial agents, and one or more trialkanolamine alkoxylate buffers are useful in contact lens care solutions for rapid disinfection of contact lenses. A disinfecting amount of antimicrobial agent is an amount that will at least partially reduce the microorganism population in the formulations employed. Preferably, a disinfecting amount is that which will reduce the microbial burden of representative bacteria by three log orders in four hours and one log for representative fungi. Most preferably, a disinfecting amount is an amount which will eliminate the microbial burden of more than 10 cfu per tested microorganism on a contact lens when used according to its regimen for the recommended soaking time as established by ISO (International Standards for Ophthalmic Optics)/FDA Stand-Alone Procedures for Disinfection Test (ISO/DIS 14729; 2001). Typically, such agents are present in concentrations ranging from about 0.00001 to about 0.5 percent weight/volume (w/v), and more preferably, from about 0.00003 to about 0.5 percent w/v. A preservative amount of antimicrobial agent in the subject compositions is that amount that prevents biologic deterioration of substances or devices with which the compositions are used. Preservative amounts of antimicrobial agent in the subject compositions is about 0.0001 to about 5.0 weight percent, more preferably about 0.001 to about 1.0 weight percent and most preferably about 0.025 to about 0.50 weight percent.

As stated above, contact lenses are cleaned without the need for manual rubbing and rapidly disinfected by contacting the lens with a solution of the present composition. Such is accomplished by simply soaking or immersing a contact lens in several milliliters of the subject solution. Preferably, the contact lens is permitted to soak in the solution for a period of at least one to four hours. The contact lens is then removed from the solution, optionally rinsed with the same or a different solution, for example a preserved isotonic saline solution and then replaced on the eye.

Solutions containing one or more compositions of the present invention may be formulated into specific contact lens care products for use as customary in the field of ophthalmology. Such products include but are not limited to wetting solutions, soaking solutions, cleaning and conditioning solutions, as well as multipurpose type lens care solutions and in-eye cleaning and conditioning solutions.

Solutions containing one or more compositions of the present invention may be formulated into specific products for disinfecting medical devices such as for example but not limited to contact lenses.

Products containing one or more compositions of the present invention may be formulated for preservation against microbial contamination such as for example but not limited to ophthalmic solutions, pharmaceuticals, artificial tears and comfort drops.

Solutions containing one or more compositions of the present invention may be formulated into specific products for preserving medical devices from microbial contamination such as for example but not limited to products formulated for the storage of contact lenses.

While the invention has been described in conjunction with specific examples thereof, this is illustrative only. Accordingly, many alternatives, modifications, and variations will be apparent to those skilled in the art in the light of the foregoing description and it is, therefore, intended to embrace all such alternatives, modifications, and variations as to fall within the spirit and scope of the appended claims.

We claim:

1. An ophthalmic composition comprising one or more antimicrobial agents selected from the group consisting of poly(hexamethylene biguanide) and polyquaternium-1; and
one or more trialkanolamine alkoxylate buffers of general formula

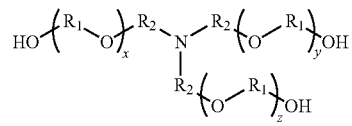

wherein the $R_1$ groups may be the same or different $C_{1-6}$ alkylene; the $R_2$ groups may be the same or different $C_{1-6}$ alkylene; and x, y and z may be the same or different selected from the group consisting of integers from 1 to 50, and the composition has a final osmotic value from 200 to 450 mOsm/kg.

2. The composition of claim 1 wherein said one or more trialkanolamine alkoxylated buffers is a triethanolamine ethoxylate where x=1-10, y=1-10 and z=1-10.

3. The composition of claim 1 further comprising one or more surfactants selected from the group consisting of poly(ethylene oxide)-poly(propylene oxide)-poly(ethylene oxide) polyethers and poly(propylene oxide)-poly(ethylene oxide)-poly(propylene oxide) polyethers.

4. The composition of claim 1 further comprising one or more tonicity agents selected from the group consisting of zinc chloride, sodium chloride, potassium chloride, dextrose, mannose, glycerin, propylene glycol, calcium chloride and magnesium chloride.

5. The composition of claim 1 further comprising one or more viscosity agents selected from the group consisting of water-soluble cellulose polymers, guar, hydroxyethyl guar, hydroxypropyl guar, hydroxypropylmethyl guar, poly(N-vinylpyrrolidone), poly(vinyl alcohol), poly(ethylene glycol), and poly(ethylene oxide).

6. The composition of claim 1 further comprising one or more wetting agents selected from the group consisting of poly(vinyl alcohol), poly(N-vinylpyrrolidone), water-soluble cellulose derivatives, poly(ethylene glycol), glycerin, propylene glycol, non-polymeric diols and non-polymeric glycols.

7. The composition of claim 1 further comprising one or more sequestering agents selected from the group consisting of ethylenediaminetetraacetic acid, gluconic acid, citric acid, tartaric acid and salts thereof.

8. The composition of claim 1 further comprising one or more carbohydrates selected from the group consisting of monosaccharides, disaccharides, oligosaccharides and polysaccharides.

9. The composition of claim 1 further comprising one or more buffers selected from the group consisting of citrate buffers and tris(hydroxymethyl)aminomethane (Tris) buffers.

10. The composition of claim 1 wherein said one or more trialkanolamine alkoxylate buffers are present from 0.02 to 3.0 percent by weight based on the total weight of the composition.

11. The composition of claim 1 wherein said one or more trialkanolamine alkoxylate buffers is a triethanolamine ethoxylate buffer with $x=1$ or 2, $y=1$ or 2 and $z=1$ or 2.

* * * * *